US011141714B2

(12) United States Patent
Hock et al.

(10) Patent No.: US 11,141,714 B2
(45) Date of Patent: Oct. 12, 2021

(54) SELECTIVE ALKANE ACTIVATION WITH SINGLE-SITE ATOMS ON AMORPHOUS SUPPORT

(71) Applicant: UCHICAGO ARGONNE, LLC, Chicago, IL (US)

(72) Inventors: Adam S. Hock, Chicago, IL (US); Neil M. Schweitzer, Evanston, IL (US); Jeffrey T. Miller, Naperville, IL (US); Bo Hu, Chicago, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 14/946,453

(22) Filed: Nov. 19, 2015

(65) Prior Publication Data
US 2016/0074838 A1 Mar. 17, 2016

Related U.S. Application Data

(62) Division of application No. 13/830,320, filed on Mar. 14, 2013, now Pat. No. 9,192,919.

(51) Int. Cl.
| | |
|---|---|
| B01J 23/755 | (2006.01) |
| B01J 23/06 | (2006.01) |
| B01J 23/08 | (2006.01) |
| B01J 23/72 | (2006.01) |
| B01J 23/745 | (2006.01) |
| B01J 23/75 | (2006.01) |
| C07C 5/32 | (2006.01) |
| C07C 5/333 | (2006.01) |
| B01J 37/02 | (2006.01) |
| B01J 37/03 | (2006.01) |
| B01J 37/06 | (2006.01) |
| B01J 37/18 | (2006.01) |
| B01J 21/08 | (2006.01) |
| B01J 35/00 | (2006.01) |
| B01J 35/02 | (2006.01) |
| B01J 35/10 | (2006.01) |
| C10G 49/02 | (2006.01) |

(52) U.S. Cl.
CPC ............ B01J 23/755 (2013.01); B01J 21/08 (2013.01); B01J 23/06 (2013.01); B01J 23/08 (2013.01); B01J 23/72 (2013.01); B01J 23/745 (2013.01); B01J 23/75 (2013.01); B01J 35/002 (2013.01); B01J 35/023 (2013.01); B01J 35/1019 (2013.01); B01J 35/1047 (2013.01); B01J 37/0201 (2013.01); B01J 37/0203 (2013.01); B01J 37/0209 (2013.01); B01J 37/0238 (2013.01); B01J 37/035 (2013.01); B01J 37/06 (2013.01); B01J 37/18 (2013.01); C07C 5/322 (2013.01); C07C 5/3332 (2013.01); C10G 49/02 (2013.01); C07C 2521/08 (2013.01); C07C 2523/06 (2013.01); C07C 2523/08 (2013.01); C07C 2523/72 (2013.01); C07C 2523/745 (2013.01); C07C 2523/75 (2013.01); C07C 2523/755 (2013.01); C10G 2300/1081 (2013.01); C10G 2400/20 (2013.01); Y02P 20/52 (2015.11)

(58) Field of Classification Search
None
See application file for complete search history.

(56) References Cited

U.S. PATENT DOCUMENTS

| | | |
|---|---|---|
| 2,279,198 A | 4/1942 | Huppke |
| 6,946,420 B2 | 9/2005 | Shih et al. |
| 7,186,669 B2 * | 3/2007 | Gole ................ B01J 23/14 257/253 |

OTHER PUBLICATIONS

Duchateau et al. Organometallics, 2007, 26, 4204-4211.*
Jiao et al. Journal of Catalysis 260, 2008, 329-341.*
Carriat et al JACS, 1998, 120, 2059-2070 (Year: 1998).*
Bhasin, et al., "Dehydrogenation and oxydehydrogenation of paraffins to olefins," Applied Caralysts A: General, 2001, vol. 221, p. 397-419.
Biscardi et al., Structure and Density of active Zn species in Zn/H-ZSM5 propane aromatization catalysts, Journal of Catalysis 179, Oct. 1, 1998, pp. 192-202.
Cavan!, et al., "Oxidative dehydrogenation of ethane and proane: How far from commercial implementation?," Catalysis Today, 2007, vol. 127, pp. 113-131.
Jiao, Ling, and John R. Regalbuto, "The Synthesis of Highly Dispersed Noble and Base Metals on Silica via Strong Electrostatic Adsorption: I. Amorphous Silica." Journal of Catalysis 260.2 (2008): 329-41. Web.
Liu, et al., "Oxidative dehyrogenation of ethane over Na2WO4—Mn/SiO2 catalyst using oxygen and carbon dioxide as oxidants," Natural Gas Conversion V, vol. 119, pp. 593-597.
R. J. Kokes, Characterization of adsorbed intermediates on zinc oxide by infrared spectroscopy, Accounts of Chemical Research, 1973, vol. 6 (7), 226-233.
Ren, et al., "Olefins from conventional heavy feedstocks: Energy use in steam cracking and alternative processes," Energy, 2006, vol. 31, pp. 425-451.
Thomas, John Meurig, Robert Raja, and Dewi W. Lewis, "Single-Site Heterogeneous Catalysts", Angewandte Chemie International Edition 44.40 (2005): 6456-482. Web.

(Continued)

Primary Examiner — Yun Qian
(74) Attorney, Agent, or Firm — Foley & Lardner LLP

(57) ABSTRACT

The present invention relates generally to catalysts and methods for use in olefin production. More particularly, the present invention relates to novel amorphously supported single-center, Lewis acid metal ions and use of the same as catalysts.

9 Claims, 12 Drawing Sheets

(56) References Cited

OTHER PUBLICATIONS

U.S. Notice of Allowance for U.S. Appl. No. 13/830,320, datd Jul. 17, 2015, 11 pages.
U.S. Office Action for U.S. Appl. No. 13/830,320, dated Mar. 26, 2014, 16 pages.
U.S. Office Action for U.S. Appl. No. 13/830,320, dated Sep. 10, 2014, 10 pages.
Cesar, L.G., et al., "Identification of a Pt3Co Surface Intermetallic Alloy in Pt—Co Propane Dehydrogenation Catalysts," ACS Catal., 2019, 9, pp. 5231-5244.
Hu, B., et al. "Isolated Fe on Silica as a Selective Propane Dehydrogenation Catalyst," ACS Catal., 2015, 5, pp. 3494-3503.
Hu, B., et al., "Selective propane dehydrogenation with single-site Co on $SiO_2$ by a non-redox mechanism," Journal of Catalysis, 322, 2015, pp. 24-37.

\* cited by examiner propane ⇌ propylene + H₂

Dehydrogenation

| Catalyst | TOR$_{550°C}$ ($10^{-3}$ sec$^{-1}$) | Selectivity |
|---|---|---|
| Fe(II) | 0.9 | 78 |
| Co(II) | 4.1 | 97 |
| Ni(II) | none[1] | |
| Cu | none[2] | |
| Zn(II) | 2.3 | 92 |

[1]Coked
[2]Metallic (350°C)

Hydrogenation

| Catalyst | TOR$_{200°C}$ (sec$^{-1}$) | Comments |
|---|---|---|
| Fe(II) | 1.1+ | Fe(II) < Fe(III) |
| Fe(III) | 5.0+ | +100°C |
| Co(II) | 0.04 | |
| Ni(II) | 0.27 | |
| Cu(II) | 2.2 | Cu(I)? |
| Zn(II) | 0.65 | |

| Catalyst or process | Conversion | Selectivity Total olefin | Selectivity propylene |
|---|---|---|---|
| Commercial thermal cracking | 20% | 80 | 42 |
| Co(II) (0.1g) | 20% | 90 | 83 |
| Co(II) (1g) | 76% |  | 87 |
| Co(II) (1g) 2 hours on stream | 65% |  | 98 |

| Determination of the Formal Co Oxidation State from the Energy of the Co Pre-Edge XANES | | |
|---|---|---|
| Sample | XANES Pre-edge Energy | Oxidation State |
| References | | |
| Co(NH₃)₆Cl₃ | 7.7101 | +3 |
| LiCoO₂ | 7.7101 | +3 |
| Co(AcAc)₃ | 7.7102 | +3 |
| Co(AcAc)₂ | 7.7097 | +2 |
| Co(Acetate)₂ | 7.7097 | +2 |
| CoCl₂ | 7.7096 | +2 |
| CoF₂ | 7.7096 | +2 |
| ClCo(PPH₃)₃ | 7.7088 | +1 |
| Co Foil | 7.7090 | (calibration) |

SELECTIVE ALKANE ACTIVATION WITH SINGLE-SITE ATOMS ON AMORPHOUS SUPPORT

CROSS-REFERENCE TO RELATED PATENT APPLICATIONS

This application is a Divisional of U.S. application Ser. No. 13/830,320, filed Mar. 14, 2013, incorporated herein by reference in its entirety.

STATEMENT OF GOVERNMENT-SPONSORED RESEARCH

This invention was made with United States government support pursuant to a contract with the following agencies: U.S. Department of Energy (Contract No. DE-AC02-06CH11357). The United States government has certain rights in the invention.

FIELD OF THE INVENTION

The present invention relates generally to olefin production. More particularly, the present invention relates to novel catalysts, and methods of making and using the same in olefin production.

BACKGROUND OF THE INVENTION

As global demand on hydrocarbon reserves has continued to increase, more efficient utilization of petroleum and gas reserves has become an important complementary strategy to the development and deployment of sustainable energy generation. Olefin production is critical for the polymer and chemical industries and is widely utilized as intermediates in the production of transportation fuels. Historically, olefin production has generally been accomplished by one of three processes: thermal cracking of alkanes at high temperatures and catalytic dehydrogenation with Pt nano-particle or Cr oxide catalyst technologies at temperatures above about 600° C. where equilibrium favors high olefin yields; or fluid catalytic cracking. For ethylene thermal cracking of ethane, LPG and heavier feedstocks continue to be the primary route. Thermal cracking of LPG or heavier feedstocks also provide significant quantities of propylene byproduct. Fluid catalytic cracking in refineries also produce significant quantities of propylene byproduct. However, over the past two decades, propylene growth rate has outpaced these conventional supply routes leading to construction of a number of commercial units for selective catalytic dehydrogenation of propane to propylene.

For alkanes with three or more carbons, thermal cracking results in mixtures of C—C and C—H cracked products. Propane, for example, produces propylene, ethylene, hydrogen, and methane. Because of the low olefin yields by thermal cracking, however, catalytic conversion processes are often favored. While propylene selectivity is higher for catalytic dehydrogenation of propane than thermal cracking, increasing the propylene selectivity, i.e., reducing the C—C cleavage reaction in favor of the dehydrogenation, remains an important catalytic goal. With catalytic dehydrogenation, there is also deposition of carbon on the catalyst surface leading to rapid loss of activity, often in a few hours, thus requiring frequent regeneration, by combustion of the carbon, or coke, and expensive process designs.

Therefore, there remains a need for catalysts with high selectivity in the conversion of alkanes to alkenes, and that are additionally long-lived with minimal decrease in activity over time.

SUMMARY OF THE INVENTION

Certain embodiments of the present invention are based on the development of methods of highly selective (>95% propylene from propane) Lewis acid catalyzed dehydrogenation of alkanes to olefins. These catalysts also affect the reverse reaction, i.e., the hydrogenation of olefins to alkanes.

In one aspect, a catalyst is provided for use in olefin production comprising one or more single-atom Lewis acid metal ions on the surface of an amorphous support, wherein said catalyst selectively cleaves C—H bonds over C—C bonds in the conversion of alkanes to alkenes. In some embodiments, the Lewis acid metal may be selected from the group consisting of Fe, Co, Zn, Ni, Ti, Sc, Zr, Hf, Ce, Ta, La, Ga, and the lanthanides, or, in preferred embodiments, selected from the group consisting of Fe, Co, Zn, and Ga. In further embodiments, the catalyst may be a heterogeneous, single-site Zn(II) catalyst, in which the tetrahedrally coordinated Zn(II), Ga(III), Co(II) and Fe(II) ion is bonded to a silica support at 3-membered ring siloxane sites.

In further embodiments, the catalyst may not be redox-active. The catalyst may, in still further embodiments, have a selectivity of greater than 75% for C—H activation, or, in further embodiments, greater than 90%, or greater than 95% selectivity. The catalyst may also, in further embodiments, retain catalytic activity for longer than 1 hour, longer than 6 hours, longer than 12 hours, or longer than 24 hours. The amorphous support may, in some embodiments, be silica or a derivative thereof, or may be selected from high surface area refractory oxide supports such as the group consisting of $TiO_2$, $ZrO_2$, $CeO_2$, $AlzO_3$, MgO, and mixtures of these.

In another aspect, the present invention provides a method of alkane dehydrogenation comprising the step of preferentially activating C—H bonds by heterolytic splitting of the bond into a surface-bound $H^+$ and a metal-C bond. The method may further comprise the step of reacting an alkane with an amorphously supported single-atom Lewis acid catalyst. In some embodiments, the Lewis acid metal may be selected from the group consisting of Fe, Co, Zn, Ni, Ti, Sc, Zr, Hf, Ce, Ta, La, Ga, and the lanthanides, or, in preferred embodiments, selected from the group consisting of Fe, Co, Zn, and Ga. In further embodiments, the catalyst may be a heterogeneous, single-site Zn(II) catalyst, in which the tetrahedrally coordinated Zn(II), Ga(III), Co(II) and Fe(II) ion is bonded to a silica support at 3-membered ring siloxane sites.

In further embodiments, the catalyst may not be redox-active. The catalyst may, in still further embodiments, have a selectivity of greater than 75% for C—H activation, or, in further embodiments, greater than 90%, or greater than 95% selectivity. The catalyst may also, in further embodiments, retain catalytic activity for longer than 1 hour, longer than 6 hours, longer than 12 hours, or longer than 24 hours. These features are improvements over the existing industrial processes for olefin production (see FIG. 9).

As used herein, a "catalyst" is any substance or material which changes the rate of conversion of alkanes to alkenes but is not, itself, consumed.

As used herein, an "olefin" or "alkene" refers to any unsaturated hydrocarbon containing one or more pairs of carbon atoms linked by a double bond. The olefins described herein include cyclic or aliphatic olefins, and include monoolefins, diolefins, triolefins, etc.

As used herein, "redox-active" refers to any material that is capable of undergoing a reaction characterized by a change in oxidation state.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All processes described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 1a illustrating propene hydrogenation and FIG. 1b illustrating propane dehydrogenation rates as a function of time for $Zn/SiO_2$ catalysts and an $SiO_2$ blank;

FIG. 2a is an X-ray absorption spectroscopy analysis of the $Zn/SiO_2$ catalyst, and FIG. 2b X-ray absorption near edge structure (XANES) of $Zn/SiO_2$;

FIG. 5a catalytic rate of propane dehydrogenation at 550° C. per/g catalyst verses time on stream and FIG. 5b selectivity towards propene as a function of time for $Zn(II)/SiO_2$ and $SiO_2$;

FIG. 6a illustration of $SiO_2$ defect site for Zn(II) binding, FIG. 6b the proposed structure of catalytically active Zn site, and FIG. 6c proposed catalytic reaction pathway and transition states for olefin hydrogenation and alkane dehydrogenation on single-site, Zn(II) Lewis acid catalyst. The reaction free energies (kcal/mol) are shown in the inset.

DETAILED DESCRIPTION OF THE PREFERRED EMBODIMENTS

Figure 1A:
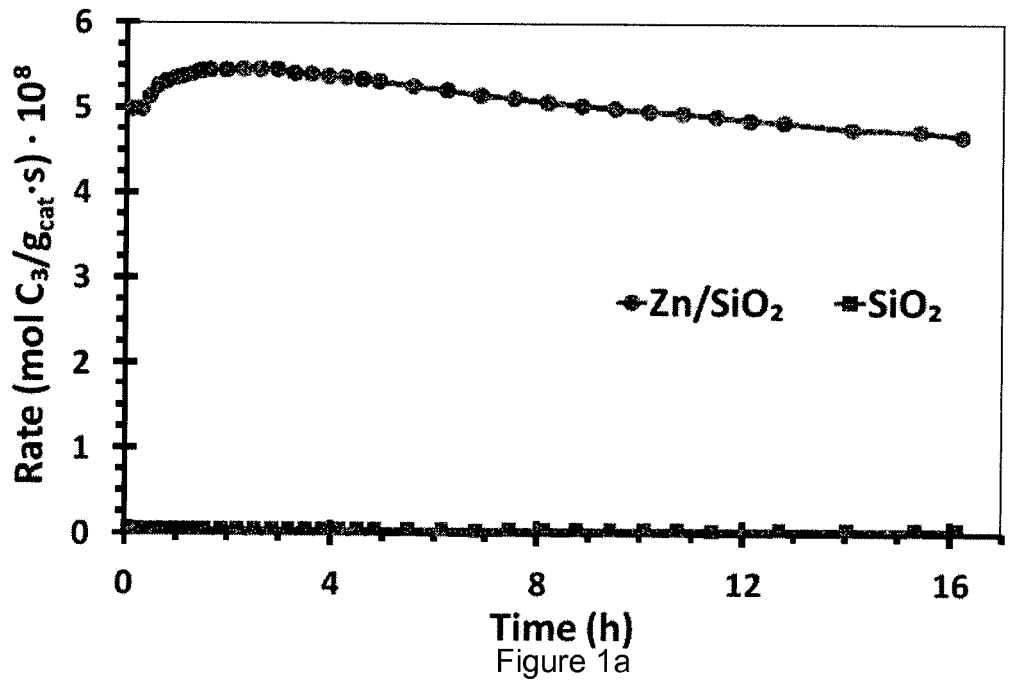
FIGS. 1a and 1b are line graphs.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

The present invention relates to olefin production. Mechanistically, olefin hydrogenation is the reverse reaction to alkane dehydrogenation and has been used as a guide for understanding dehydrogenation catalysts. For homogeneous catalysts the mechanistic steps for olefin hydrogenation have been extensively studied. Active hydrogenation catalysts generally activate $H_2$ by an oxidative addition mechanism where the metal center transfers two electrons into the anti-bonding orbital of $H_2$, resulting in homolytic dissociation on metal surfaces and oxidative addition at a single metal center. The olefin inserts into one of the resulting hydride ligands, followed by the reductive elimination of the now saturated alkane concomitant with two electron reduction of the catalytic site. Thus, most homogeneous hydrogenation catalysts are transition metal ions with several stable oxidation states that are readily accessible under catalytic conditions. Extension of this mechanism to dehydrogenation catalysts is difficult because homogeneous catalysts are not typically stable at high the temperature where the reaction is thermodynamically favored. For catalytic data describing both reactions, hydrogenation and dehydrogenation, with the claimed catalysts, see FIG. 7. Several $H_2$ removal strategies have been used to drive the reaction under milder conditions. While $H_2$ transfer strategies are valuable for mechanistic studies, this approach is not viable for large scale olefin production. Moreover, most hydrocarbon activation studies rely upon the well-established redox paradigms of C—H bond activation.

Similarly, for heterogeneous catalysts, the surface atoms in the metallic nano-particles, for example, on zero valent Pt, dissociate C—H bonds. At the high reaction temperatures, two hydrogen atoms combine on the surface and desorb to produce $H_2$ while the dehydrogenated alkane leaves the surface as an olefin. At the reaction conditions, there is also dissociation of C—C bonds leading to lower molecular weight, unwanted by-products, like methane and ethane from propane. In addition, the loss of several hydrogen atoms leads to carbon deposits on the catalyst surface and loss of activity.

In one embodiment, catalysts for use in the present invention comprise a Lewis acid. Specifically, certain implementations comprise a non-reducible Lewis acid metal ion, including but not limited to Lewis acids (LA) do not change oxidation state during reaction. LA's typically coordinate to an electron lone pair in molecules, often to halide and oxygen atoms, generating a partial positive charge at the adjacent carbon and accelerating the reactivity at this carbon atom. Prominent examples of LA catalysis include the Friedel-Crafts acylation of aromatics, aldol cross coupling reactions, Diels-Alder cycloaddition, olefin polymerization, and many other organic reactions. For organic reactions, often Lewis Acid catalysts are highly sensitive to traces of water and other strongly coordinating solvents. In contrast to the above reactions, there are few examples where Lewis acids react with the electron pair in sigma bonds, although "frustrated" Lewis acid/base pairs (FLP) can heterolytically dissociate $H_2$ and are active for imine and olefin hydrogenation. Given the microscopic reversibility of hydrogenation and dehydrogenation reactions, heterogeneous LA's were discovered herein to catalyze olefin hydrogenation and alkane dehydrogenation at elevated temperatures. It is believed that the Lewis acid catalysts proceed through a reaction pathway that catalyzes the heterolytic disassociation of the C—H sigma bonds in alkane dehydrogenation and the H—H sigma bonds in olefin hydrogenation, i.e. that the process pathway does not involve a redox reaction. In one embodiment, the Lewis acid catalysts comprise a single-site structure which exists in a single oxidation state are structurally and kinetically stable at high reaction temperatures and have high alkane dehydrogenation selectivity are contemplated by the present invention, including but not limited to Zn, Fe, Co, Ga, Ni, Ti, Sc, Zr, Hf, Ce, Y, Ta and La as well as the lanthanides. In preferred embodiments, the metal-ions are selected from the group consisting of Zn, Fe, Co and Ga.

Figure 7:
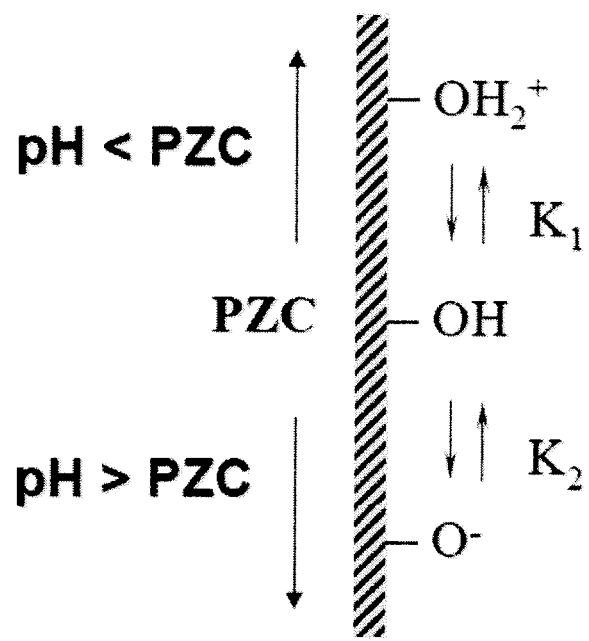
FIG. 7 is a schematic showing catalyst synthesis, wherein Co(III) cation is adsorbed onto an amorphous $SiO_2$ support.
Figure 8:
FIG. 8 is a set of two tables showing the catalytic results for a series of catalysts in both dehydrogenation and hydrogenation.
Figure 9:
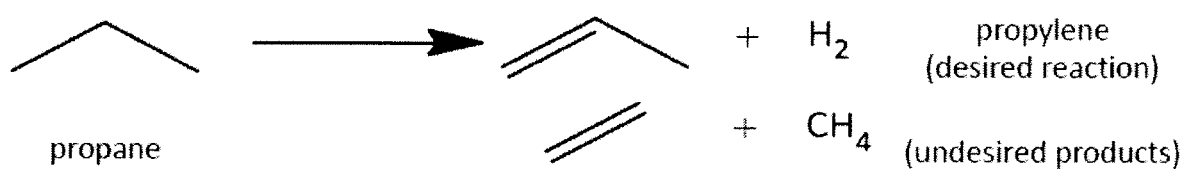
FIG. 9 is a table showing a comparison of properties of the claimed catalysts with traditional industrial methods of olefin production, in three categories: conversion, selectivity for olefins, and selectivity for propylene.

The catalyst further comprises a support material. In one embodiment, the support material is a high surface area refractory oxide, such as, but not limited to, silica, alumina, cerium oxide, titanium oxide, magnesium oxide, zirconium oxide, aluminum-phosphate, MCM-41, SBA-15, zeolites, and other oxides. In one embodiment, the support material is amorphous. The amorphous support may be selected from any amorphous material. In a preferred embodiment, the amorphous support may be SiO2 or $TiO_2$. In those embodiments, the hydroxyl groups may be deprotonated with a base allowing for a cation complex to be adsorbed as an ion pair, as shown in the schematic of FIG. 7. Under catalytic conditions of dehydrogenation the supports are thermally stable and do not have catalytic activity of their own.

In some embodiments, the catalyst is a heterogeneous, single-site Zn(II), Ga(III), Co(II) or Fe(II) catalyst, in which the tetrahedrally coordinated Zn(II) ion, or other ions are bonded to a silica support at 3-membered ring siloxane sites. Under reaction conditions, although there is no change in oxidation state, and additionally there may be loss of one ligand, leading to a coordinatively unsaturated catalytic site. Density functional theoretical modeling supports the hypothesis that the Lewis acid Zn(II) site is activating the C—H sigma bond by a non-oxidative, heterolytic bond cleavage pathway, rather than by a redox mechanism typical of transition metals. Lewis acid hydrogenation and dehydrogenation catalysis represents a new opportunity for hydrocarbon transformations.

The reactions described herein may take place at any temperature necessary to facilitate a high conversion of olefins, and will depend upon the starting alkane and the desired olefin product. For example, the reaction may take place at 600° C., 650° C., 700° C., 750° C., 800° C., 850° C., 900° C., 950° C., or 1000° C. Generally, high conversion of olefins is only possible at a high temperature, and, for the purposes of commercial manufacture, a high temperature is desirable as it leads to higher production rates.

The catalysts described herein may be used in any suitable reactor. The process could utilize a series of fixed bed reactors, where each reactor could be independently regenerated, a moving bed reactor where the catalysts moves through the reactor and is regenerated in a separate section of the plant, or a fluid bed reactor, where the catalyst is circulated through the reactor and regenerated in a separate vessel. Furthermore, the catalysts described herein may be regenerated using methods well-known in the art to restore selectivity and activity after use to remove coking.

The invention will now be described in greater detail by reference to the following non-limiting examples.

EXAMPLES

Example 1

Synthesis of Representative Catalysts

Iron on silica catalysts, two embodiments of which are described in greater detail below, as Catalysts "A" and "B," were generally synthesized using an organometallic precursor. The precursor, 2,4-dimethyl-1,3-pentadienide iron(II), is very reactive with hydroxyl groups inherently present on $SiO_2$ and $TiO_2$ support surfaces with high surface area. The precursor was synthesized as follows: $MgBr_2$ was dissolved with THF in a round bottom flask. The solution was kept cold, and the cold THF solution of potassium pentadienide was added dropwise. The reaction mixture was stirred for two hours at room temperature, then cooled and added dropwise into anhydrous $FeCl_2$THF solution. It was stirred for two hours at room temperature and a deep red solution was obtained. It was vacuumed to evaporate THF and extract the product with pentane. The pentane extraction was filtered and the pentane was evaporated by vacuum to yield the iron precursor. The iron complex may also be purified further by sublimation.

The synthesis was performed under air and moisture-free conditions simply by mixing the precursor solution with $SiO_2$ in hexane. After the solvent had evaporated, the remaining powder was reduced in 4% $H_2$/He at 350° C. The structure of the catalysts was confirmed by X-ray absorption spectroscopy (XAS) at the Advanced Photon Source (APS) of Argonne. Extended X-ray absorption fine structure (EX-AFS) results confirm that the supported catalyst precursor is a single-atom Fe(II) with 5 Fe—O (or Fe—C) bonds at an average bond distance of 1.97 Å. After treatment in $H_2$ at 350° C., there is a loss of the organic ligand and generation of the redox-active single-atom Fe(II) site. This redox-active Fe(II) site has been shown to reversibly undergo oxidation with air to Fe(III) (with 5 Fe—O bonds at 1.86 Å) and can be reduced back to Fe(II) with hydrogen or propane. If, however, the supported organometallic Fe precursor is first oxidized in air, the resulting Fe(III) site is not redox active. Similarly, attempts to prepare the catalyst from more stable organometallic Fe precursors, such as ferrocene, did not lead to redox-active, single-atom Fe structures. Thus, the structure of the transition metal precursor, methods of support deposition, and subsequent pretreatment steps all affect the structure and reactivity of the catalyst.

Two representative iron catalysts were obtained as follows: 2,4-dimethyl-1,3-pentadienide iron pentane solution was added to dry silica in a 50 ml flask. The mixture was stirred for 3 hours at room temperature. The pentane solvent was evaporated and the greenish solid was obtained. Catalyst A, "Reduced" $Fe/SiO_2$, as shown in Table 2, was obtained when the 2,4-dimethyl-1,3-pentadienide iron on silica catalyst was treated with $H_2$ without being exposed to air at temperatures from 350-500° C. Catalyst B, the "Oxidized" $Fe/SiO_2$, as shown in Table 2, was obtained when the 2,4-dimethyl-1,3-pentadienide iron on silica was exposed to air at room temperature directly after it's synthesized.

Cobalt catalysts (were synthesized using the strong electrostatic adsorption methodology. About 20 g of silica support was suspended in a large excess of deionized water. The pH of the solution was adjusted to 10 using ammonium hydroxide. In a separate flask, an appropriate amount of the zinc nitrate or cobalt nitrate precursor, equivalent to a 4% wt catalyst, was dissolved in a large excess of deionized water. The two solutions were mixed. The pH of the final solution was adjusted to 10 with $NH_3OH$, at which point the solution turned clear and colorless. This solution was allowed to rest for 45 min. The resulting powder was filtered and rinsed several times with deionized water. Finally, the powder was dried overnight in air at 125° C. and subsequently calcined in air at 300° C. for 3 h. Again, the structures of the catalysts we confirmed by XAS. The oxidation state of the metals was always 2+, even under $H_2$ at 400° C. Under hydrogenation and dehydrogenation conditions, the single site structure was preserved.

Representative cobalt catalysts (Catalysts C, D, E, and F) were obtained as follows: Catalyst C, $Co/SiO_2$ made from $Co(III)(NH_3)_6Ch$, started with 20 g of $SiO_2$ (Davisil 646, 35-60 mesh, 300 $m^2/g$ and 1.1 cc/g, Aldrich) and was suspended in approximately 200 mL deionized water. The pH of the solution was adjusted to about 11 using concentrated ammonium hydroxide ($NH_4OH$). In a separate flask, 5 g $Co(NH_3)_6Ch$, Aldrich), which is in excess of what can be adsorbed onto the support surface, was dissolved in 50 mL of deionized water and the pH was also adjusted to 11 using ammonium hydroxide. The basic Co(III) solution was rapidly added to the silica with stirring for 10 min at RT. The solid was allowed to settle for 5 minutes and the solution decanted. 200 mL of $H_2O$ was added and stirred for 10 min. The solid was settled and the water decanted. The resulting wet powder was vacuum filtered and rinsed several times with deionized water, dried at RT and then overnight in air at 125° C. and subsequently calcined in air with a 1 hour ramp to 300° C., maintained for 3 hours at 300° C., and 1 hour cool to ambient temperature. The elemental composition was determined by ICP, 2.1%.

Catalyst D, $Co/SiO_2$ made from $Co(II)(NO_3)_3 \cdot 6H_2O$, started with 20 g of $SiO_2$ suspended in approximately 200 mL deionized water. The pH of the solution was adjusted to about 11 using concentrated ammonium hydroxide ($NH_4OH$). In a separate flask, 5 g Co(II) nitrate ($Co(NO_3)_2 \cdot 6H_2O$, Aldrich), which is in excess of what can be adsorbed onto the support surface, was dissolved in 50 mL of deionized water and the pH was also adjusted to 11 using ammonium hydroxide. Initially, the Co(II) solution precipitated. Continued addition of $NH_4OH$ lead to partial dissolution of the precipitate; however a small amount remained. The basic Co(II) solution was filtered and the clear solution was added to the silica with stirring for 10 min at RT. The solid was allowed to settle for 5 minutes and the solution decanted. 200 mL of $H_2O$ was added and stirred for 10 min. The solid was settled and the water decanted. The resulting wet powder was vacuum filtered and rinsed several times with deionized water, dried at RT and then overnight in air at 125° C. and subsequently calcined in air with a 1 hour ramp to 300° C., maintained for 3 hours at 300° C., and 1 hour cool to ambient temperature. The elemental composition was determined by ICP, 3.09%.

Catalyst E, $Co/SiO_2$ made from formic acid, began with 5 g of $SiO_2$ suspended in approximately 200 mL deionized water. The pH of the solution was adjusted to about 10 using concentrated ammonium hydroxide ($NH_4OH$). In a separate flask, Co(II) nitrate ($Co(NO_3)_2 \cdot 6H_2O$, Aldrich), which is in excess of what can be adsorbed onto the support surface, was dissolved in 50 mL of deionized water with two equivalents of formic acid then the pH was also adjusted to 11 using ammonium hydroxide. The Co(II) solution remained homogeneous. The basic Co(II) solution was added to the silica with stirring for 10 min at RT. The solid was allowed to settle for 5 minutes and the solution decanted. The solid was settled and the water decanted. The resulting wet powder was vacuum filtered and rinsed several times with deionized water, dried at RT and then overnight in air at 125° C. and subsequently calcined in air with a 1 hour ramp to 300° C., maintained for 3 hours at 300° C., and 1 hour cool to ambient temperature. The elemental composition was determined by ICP, 1.12%.

Catalyst F, $Co/SiO_2$ made with citric acid, was synthesized beginning with 10 g of $SiO_2$ was suspended in approximately 50 mL deionized water. The pH of the solution was adjusted to about 11 using concentrated ammonium hydroxide ($NH_4OH$). In a separate flask, 2 g Co(II) nitrate ($Co(NO_3)_2 \cdot 6H_2O$, Aldrich), which is in excess of what can be adsorbed onto the support surface, was dissolved in 50 mL of deionized. Approximately, 1 g of citric acid was dissolved in the Co(II) solution. The pH was also adjusted to 11 using ammonium hydroxide. In the presence of citric acid the Co(II) did not precipitate. The basic Co(II)-citric acid solution was added to the silica with stirring for 10 min at RT. The solid was allowed to settle for 5 minutes and the solution decanted. 100 mL of $H_2O$ was added and stirred for 10 min. The solid was settled and the water decanted. The resulting wet powder was vacuum filtered and rinsed several times with deionized water, dried at RT and then overnight in air at 125° C. and subsequently calcined in air with a 1 hour ramp to 300° C., maintained for 3 hours at 300° C., and 1 hour cool to ambient temperature.

Zn on silica catalysts (described in further detail below) were generally synthesized using the strong electrostatic adsorption methodology. 25 g of silica support ($SiO_2$, Davisil 646, 35-60 mesh, 300 $m^2/g$ and 1.1 cc/g, Aldrich) was suspended in approximately 200 mL deionized water. The pH of the solution was adjusted to about 11 using concentrated ammonium hydroxide ($NH_4OH$). In a separate flask, 5 g zinc nitrate ($Zn(NO_3)_2 \cdot 6H_2O$, Aldrich), which is in excess of what can be adsorbed onto the support surface, was dissolved in 50 mL of deionized water and the pH was also adjusted to 11 using ammonium hydroxide. Initially, the Zn solution precipitated, but continued addition of $NH_4OH$ gave a clear solution. The basic Zn solution was rapidly added to the silica with stirring for 10 min. The solid was allowed to settle for 5 minutes and the solution decanted 200 mL of $H_2O$ was added and stirred for 10 min. The solid was settled and the water decanted. The resulting wet powder was vacuum filtered and rinsed several times with deionized water, dried overnight in air at 125° C. and subsequently calcined in air with a 1 hour ramp to 300° C., maintained for 3 hours at 300° C., and 1 hour cool to ambient temperature. The Zn loading was 3.88% and was determined by Galbraith Laboratories, Inc. (Knoxville, Tenn.) using inductively coupled plasma atomic emission spectroscopy.

Catalyst G, having a pH of 10, was obtained when a silica support (Davisil 646, Aldrich) was suspended in the deionized water. The pH of the solution was adjusted to about 10 using concentrated ammonium hydroxide ($NH_4OH$). In a separate flask, zinc nitrate ($Zn(NO_3)_2 \cdot 6H_2O$, Aldrich), which is in excess of what can be adsorbed onto the support surface, was dissolved in deionized water and the pH was also adjusted to 10 using ammonium hydroxide. The basic Zn solution was rapidly added to the silica with stirring for 10 min. The solid was allowed to settle for 5 minutes and the solution decanted. The resulting wet powder was vacuum filtered and rinsed several times with deionized water, dried at 125° C. and subsequently calcined in for 3 hours at 300° C. Catalyst H, having a pH<10 was obtained using a similar synthetic procedure as Catalyst G, however, without addition of $NH_4OH$. As a result, the pH of synthesis solution was less than 10 (pH=5). Catalyst I, having a pH>10, was obtained using a similar synthetic procedure as Catalyst G and H, however, the pH of synthesis solution was more than 10 (pH=11).

Representative zinc catalysts were obtained as follows: Catalyst J, $Zn/SiO_2$ made with Incipient Wetness Impregnation (IWI) method. Catalyst K, $Ni/SiO_2$, was made using a similar synthetic procedure as Catalyst G. The only difference was that the precursor of catalyst synthesis was $Ni(NO_3)_2 \cdot 6H_2O$.

Representative nickel catalysts were obtained as follows: Catalyst K, $Ni/SiO_2$, was created using a similar synthetic procedure as Catalyst G. The only difference was that the precursor of catalyst synthesis was $Ni(NO_3)_2 \cdot 6H_2O$. Catalyst L, or $Cu/SiO_2$, used a precursor of $Cu(NO_3)_2 \cdot 6H_2O$.

Representative gallium catalysts were obtained as follows: Catalyst M, $Ga/SiO_2$, was synthesized using the strong electrostatic adsorption methodology. Silica support (Davisil 646, Aldrich) was suspended in the deionized water. The pH of the solution was adjusted to about 10 using concentrated ammonium hydroxide ($NH_4OH$). In a separate flask, Gallium nitrate ($Ga(NO_3)_3 \cdot xH_2O$, Aldrich), which is in excess of what can be adsorbed onto the support surface, was dissolved in deionized water. The excess amount of citric acid wad added into the solution and the pH was also adjusted to 10 using ammonium hydroxide. The basic Ga solution was rapidly added to the silica with stirring for 10 min. The solid was allowed to settle for 5 minutes and the solution decanted. The resulting wet powder was vacuum filtered and rinsed several times with deionized water, dried at 125° C. and subsequently calcined in for 3 hours at 300° C. Catalyst N, $Ga/SiO_2$ (IWI), was synthesized using the incipient wetness impregnation methodology. 3.0 g gallium nitrate ($Ga(NO_3)_3 \cdot xH_2O$, Aldrich) was dissolved in 10 ml deionized water and one equivalent of citric acid wad added into the solution and the total volume of solution was adjusted to 20 ml while keeping pH to 10 by using ammonium hydroxide. The basic Ga solution was added to the 20 g silica dropwise while stirring to mix well. The resulting wet powder was vacuum filtered and rinsed several times with deionized water, dried at 125° C. and subsequently calcined in for 3 hours at 300° C.

Example 2

Catalytic Performance Testing

Catalyst performance testing was conducted in a vertical, quartz tube reactor equipped with mass flow controllers and the products were determined by on-line gas chromatography (50 m GS-Alumina capillary column). Approximately 1 g of catalyst was supported on quartz wool with an internal thermal couple placed at the top of the catalyst bed. Initially, the catalyst was purged with He (99.999%, Airgas USA, LLC), which had been further purified with an oxygen trap, at 300 mL/min at room temperature and then for 15 min at about 100° C. Then, the temperature of the reactor was raised to the reaction temperature (200° C. for hydrogenation, 550° C. for dehydrogenation) and given 2-3 hours for the temperature to stabilize.

For the propylene hydrogenation reaction, the reaction mixture was 88 mL/min of 4% $H_2$/Ar mixture and 16 mL/min 4% propene/Ar giving a contact time of about 0.9 sec. For the propane dehydrogenation reaction, the reaction mixture was 3% propane/Ar at 55 mL/min, or a contact time of 0.45 sec. Generally the conversions were under differential conditions, i.e., less than 10%; however, the flow rate and temperature were also varied to obtain higher conversions. Product composition was determined by gas calibration standards and analyzed by a flame ionization detector (FID) using $H_2$ (99.999%, Airgas USA, LLC) and air (<2 ppm $H_2O$, Airgas USA, LLC). Isopropanol catalyst poisoning experiments were conducted by loading the catalyst into a round bottom flask sealed with a septum. The flask was then attached to a Schlenk line, at less than 2 torr pressure and heated to 160° C. After evacuation and without opening to air, a predetermined amount of isopropanol, or pyridine, was injected into via syringe to the flask through the septum where it vaporized and adsorbed to the catalyst surface over one hour. The catalyst was then loaded into the quartz reactor tube (in air) and tested as described above.

In situ XAFS measurements were performed as follows: at the Zn K-edge (9.659 keV) X-ray absorption measurements were conducted on the bending magnet beamline of the Materials Research Collaborative Access Team (MR-CAT, 10-BM) at the Advanced Photon Source (APS), Argonne National Laboratory. Ionization chambers were optimized at the mid-point of the Zn spectrum for the maximum current with linear response (ca. $10^{10}$ photons detected $sec^{-1}$) using 5% Ar in $N_2$ (15% absorption) in the incident X-ray detector and a mixture of ca. 25% Ar in $N_2$ (70% absorption) in the transmission X-ray detector. A third detector in the series simultaneously collected a Zn foil reference spectrum with each measurement for energy calibration. A cryogenically cooled double-crystal Si(111) monochromator was used and detuned to 50% in order to minimize the presence of harmonics. The X-ray beam was 0.5×1.5 mm and data was collected in transmission geometry in 10 min in step scan mode. The catalyst was pressed into a 4 mm self-supporting wafer and placed in a stainless steel holder. The reactor consisted of a straight quartz tube (1"OD, 10" length) with an Ultra-Torr® fitting equipped with shut-off valves. At both ends of the reactor were Kapton windows were sealed with O-rings. The reactor has an internal thermocouple at the sample which controls the clam shell furnace. The catalyst was tested at room temperature after synthesis, in flowing H$_2$/propylene/He (100 cc/min) at 200 C and propane/He at 550 C. After measurements at elevated temperature the catalysts were cooled in the flowing gas and re-measured at room temperature without exposure to air.

X-ray absorption analysis was performed as follows: the Zn K-edge XANES energy was determined from the inflection point of the leading edge, by determination of the energy of the maximum in the first peak of the first derivative. EXAFS fits of the Zn/silica catalysts were determined from experimental phase shift and backscattering amplitudes, which were obtained from the ZnO (3 Zn-0 at 1.97 Å and 1 Zn-0 at 1.99 Å). Standard procedures based on WINXAS 3.1 software were used to fit the XAS data. The EXAFS coordination parameters were obtained by a least square fit in r-space of the first shell nearest neighbor, k$^2$-weighted Fourier transform data.

Computational Methods: First-principles calculations based on the Moller-Plesset perturbation theory (MP2) were performed to understand the binding of Zn on silica surface as well as the catalytic mechanism of propane dehydrogenation and propylene hydrogenation. The surface is represented using a cluster model consisting of localized siloxane rings of different sizes, which structurally resemble surface sites that have been identified on silica surfaces. The electronic effect on amorphous silica is mostly local; therefore, cluster models are reasonably accurate for studying chemical reactions. The structure optimizations and free energy calculations of different reaction intermediates and transition states are performed using the Gaussian-09 quantum chemistry software. The accuracy of the transition state (TS) calculations was verified by performing the intrinsic reaction coordinate (IRC) scan and frequency analysis. Natural bond orbitals (NBO) analyses were performed to obtain information about atomic charges and molecular orbitals (MO). TZVP basis sets were used to perform all the calculations (MP2/TZVP).

Figure 1B:
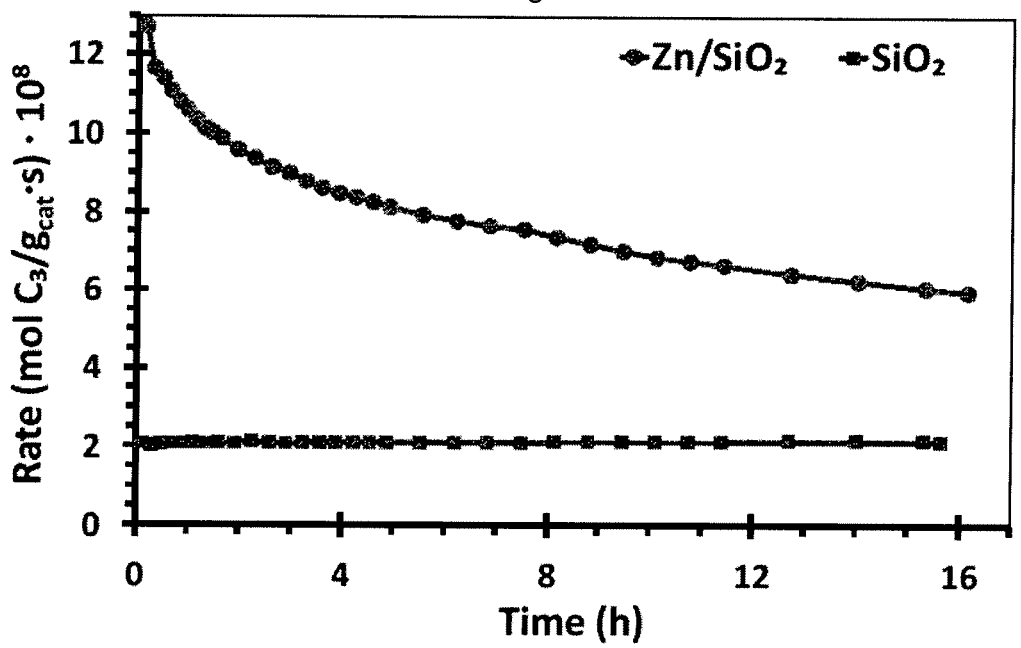

The catalytic results for the different catalysts are shown in tables 1 and 2, infra. The Fe catalysts showed enhanced activity for propylene hydrogenation, while all three catalysts were reasonably active for propane dehydrogenation. Additionally, all three catalysts showed enhanced dehydrogenation selectivity towards propene (as opposed to cracking products methane and ethylene), well above the selectivity for thermal cracking of propane. Stability tests, presented in FIG. 1, for Zn illustrate the long life of the catalyst. Although the Zn catalyst deactivates to about half the initial rate after 16 h, this lifetime easily exceeds the lifetime of noble metal, nano particle catalysts which is typically on the order of minutes.

TABLE 1

Rates and selectivities for propene hydrogenation (200° C.) and propane dehydrogenation (550° C.) for the different catalysts

| Catalyst | Oxidation St. | Hydrogenation Rate (mol C$_3$$^=$/g$_{cat}$ · s) × 10$^8$ | Dehydrogenation Rate (mol C$_3$/g$_{cat}$ · s) × 10$^8$ | Dehydrogenation Selectivity (%) |
|---|---|---|---|---|
| Co/SiO$_2$ | 2+ | 0.01 | 7.6 | 97 |
| Zn/SiO$_2$ | 2+ | 4.8 | 6.4 | 95 |
| Ga/SiO$_2$ | 3+ | 8.1 | 46 | 94 |

TABLE 2

Catalytic ability for propane dehydrogenation by different catalysts

| Catalysts | Reaction temperature | Propane conversion | Total olefin selectivity | Propylene selectivity |
|---|---|---|---|---|
| "Reduced" Fe/SiO$_2$ (A) | 550° C. | 5% | 70% | 40% |
| "Oxidized" Fe/SiO$_2$ (B) | 550° C. | — | — | — |
| Co/SiO$_2$ (C) (made from Co(II)(NH$_3$)$_6$Cl$_3$) | 550° C. | 10% | 97% | 95% |
| | 650° C.* | 38% | 86.5% | 75% |
| Co/SiO$_2$ (D) (made from Co(II)(NO$_3$)$_3$ 6H$_2$O)) | 550° C. | 20% | 98% | 95% |
| | 650° C. | 65% | 91% | 81% |
| Co/SiO$_2$ (E) (pH 10-formic acid) | 550° C. | 6% | 98.8% | 97% |
| Co/SiO$_2$ (F) (pH 10-citric acid) | 550° C. | — | — | — |
| Zn/SiO$_2$ (G) (pH 10-NH$_4$OH) | 550° C. | 6% | 97% | 94% |
| Zn/SiO$_2$ (H) (pH 5) | 550° C. | 0.3% | 68% | 37% |
| Zn/SiO$_2$ (I) (pH 11-NH$_4$OH) | 550° C. | 3% | 95% | 90% |
| Zn/SiO$_2$ (J) (IWI method) | 550° C. | 5% | 96% | 91% |
| Ni/SiO$_2$ (K) (pH 10-NH$_4$OH) | Coke Deactivation | | | |
| Cu/SiO$_2$ (L) (pH 10-NH$_4$OH) | Reduced to metallic Cu | | | |
| Ga/SiO$_2$ (M) (pH 10-citric acid) | 550° C. | 20% | 97% | 95% |
| | 650° C. | 62% | 86% | 69% |
| Ga/SiO$_2$ (N) (IWI-citric acid) | 550° C. | 31% | 97% | 94% |

The above results demonstrate that Co, Fe, Ga and Zn on silica are effective for catalytic dehydrogenation of propane to propylene. These catalysts have been tested for periods up to 24 h with little deactivation. Characterization of the Fe, Co and Zn (see Ex. 3 below) show that the catalysts are not reduced to metal as is typical of metallic Pt. In addition, the structure of the catalytic sites is a single metal ion bound to the oxide support, unlike Cr oxide and other transition metal catalysts. These effective catalysts are characterized by the positive oxidation state under reaction conditions, single ion structure and vacant coordination site, i.e., a Lewis acid center. Lewis acids are characterized by adsorption of pyridine, which gives distinctive bands in the infrared spectrum.

Figure 2A:
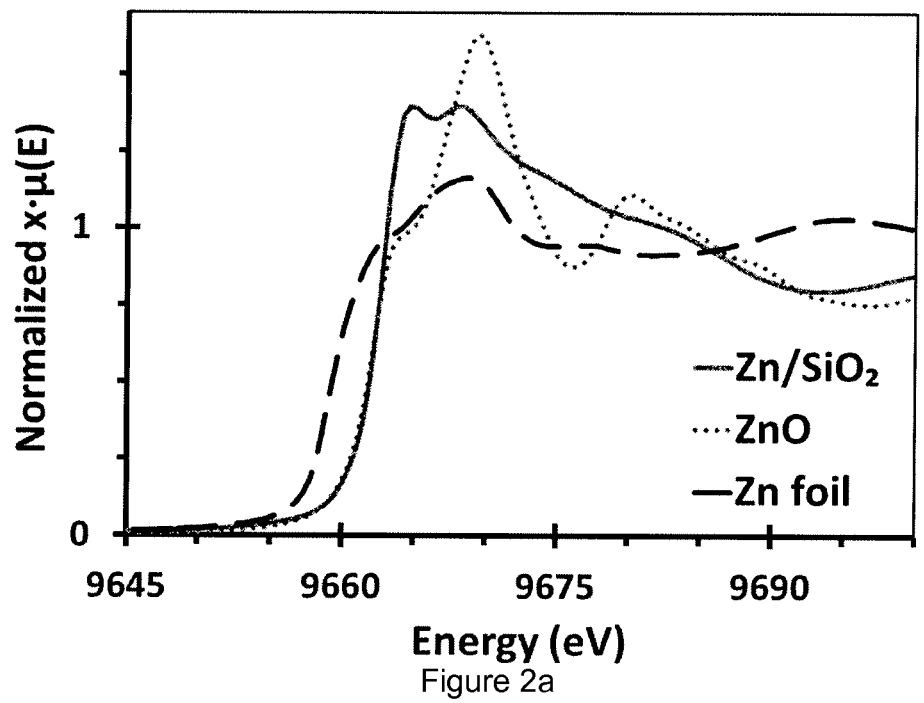
FIGS. 2a and 2b are line graphs.
Figure 2B:
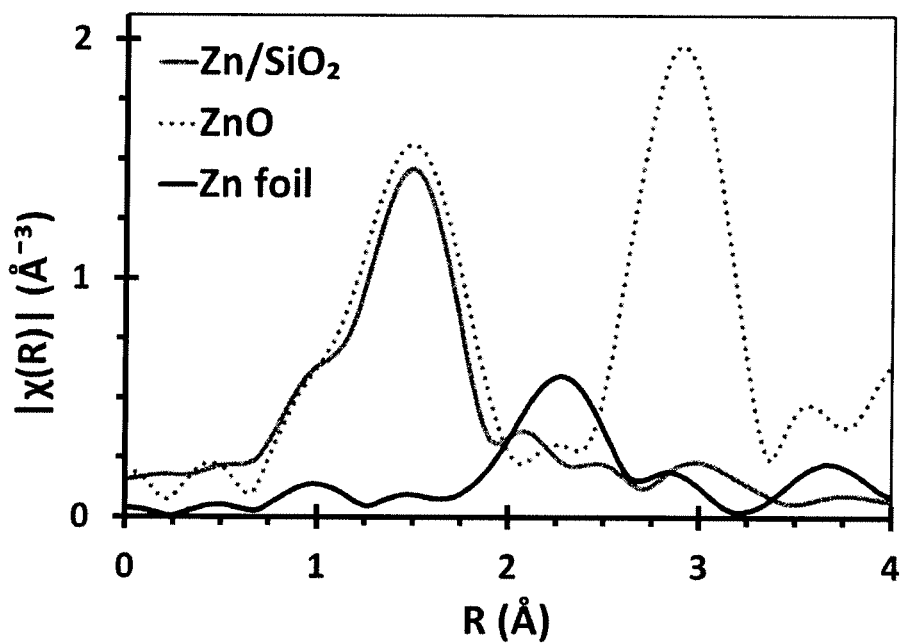
Figure 10:
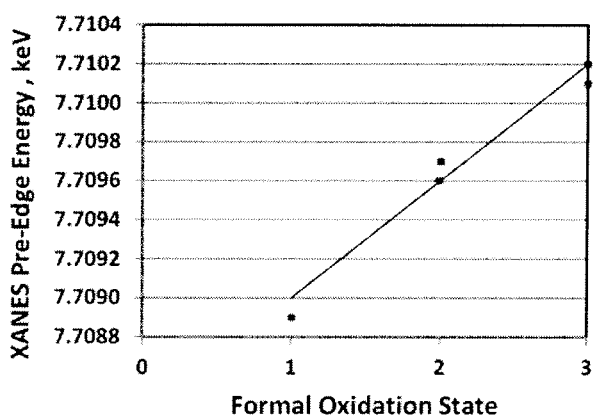
FIG. 10 is a table and line graph showing the Determination of the Formal Co-Oxidation State as determined by the Energy of the Co Pre-Edge XANES.

The oxidation state and structure of the catalyst was determined by in situ X-ray absorption spectroscopy, using the methods described above, of the as-prepared material as well as under various catalytic conditions. FIG. 2 shows the X-ray absorption near edge structure (XANES) compared to ZnO powder and Zn foil. The edge energy of the XANES determined from the inflection point of the leading edge of the Zn/SiO$_2$ indicates that the Zn sites are in the 2+ oxidation state and have an edge energy similar to the reference compounds of ZnO and Zn(II) acetate, as shown in Table 2. FIG. 10 shows the determination of the oxidation state.

The XAS of all catalytic reactions were measured at high temperature; however, thermal disorder makes precise fitting of the coordination number and bond distance less accurate at high temperature. Thus, the samples were cooled to room temperature in order to determine the changes in structure that occur at catalytic conditions

TABLE 3

| Treatment | Edge Energy, keV | N$_{zn-O}$ | R, Å | Δσ$^2$ (×10$^3$) | Eo, eV |
|---|---|---|---|---|---|
| As prepared, RT | 9.6630 | 4.0 | 1.95 | 1.0 | −1.6 |
| He 200° C., He RT | 9.6630 | 3.7 | 1.94 | 1.0 | −1.7 |

TABLE 3-continued

| Treatment | Edge Energy, keV | $N_{Zn-O}$ | R, Å | $\Delta\sigma^2$ (×10³) | Eo, eV |
|---|---|---|---|---|---|
| H2 200° C., | 9.6630 | 3.7 | 1.94 | 1.0 | −1.7 |
| $H_2 + C_3H_6$ 200° C., He | 9.6630 | 3.7 | 1.94 | 1.0 | −1.8 |
| 450° C. He, He RT | 9.6626 | 3.1 | 1.93 | 1.0 | −1.6 |
| C3H8 550° C., He RT | 9.6626 | 3.1 | 1.93 | 1.0 | −1.7 |
| C3H8 550° C. | 9.6626 | 2.9 | 1.92 | 6.0 | −3.0 |
| References | | | | | |
| ZnO | 9.6623 | 4.0 | 1.98 | 0.0 | −0.3 |
| Zn Acetate | 9.6646 | | | | |
| Zn Foil | 9.6590 | | | | |

In-situ XANES studies at reaction temperatures under oxidizing ($O_2$), reducing ($H_2$ or propane), and inert (He) all show that the zinc remains in the 2+ oxidation state. As the temperature increases above about 450° C., there is a small shift in the edge energy, ca, 0.4 eV, and change in the white line intensity indicating change in the local Zn(II) coordination, FIG. 2a. The XAS of all catalytic reactions were measured at high temperature; however, thermal disorder makes precise fitting of the coordination number and bond distance less accurate at high temperature. Thus, the samples were cooled to room temperature in order to determine the changes in structure that occur at catalytic conditions. The XANES were identical at RT and high T, indicating the structure of the catalyst was unchanged. After catalyst synthesis, there are 4 Zn—O bonds at 1.94 Å, slightly shorter than those in bulk ZnO, see the first shell peak in FIG. 2b and Table 2. Under propylene hydrogenation conditions, e.g. 200° C., the coordination number decreases slightly to 3.7 suggesting the loss of about 10% of the Zn—O bonds at 200° C. Under propane dehydrogenation (and temperatures above about 450° C.) there is a decrease in the number of bonds to 3 Zn—O with a bond distance similar to that in the starting catalyst (1.93 Å), FIG. 2b. In the as prepared catalyst, there is a very small higher shell peak (at a phase uncorrected distance of about 2.5-3.5 Å), which is consistent with isolated Zn(II) cations on the $SiO_2$ surface, but the size and disorder in this feature is too small to fit reliably. Even after heating at temperatures up to 700° C., there is no observable increase in the size of the higher shell peaks indicating high thermal stability of the surface structure.

Figure 3:
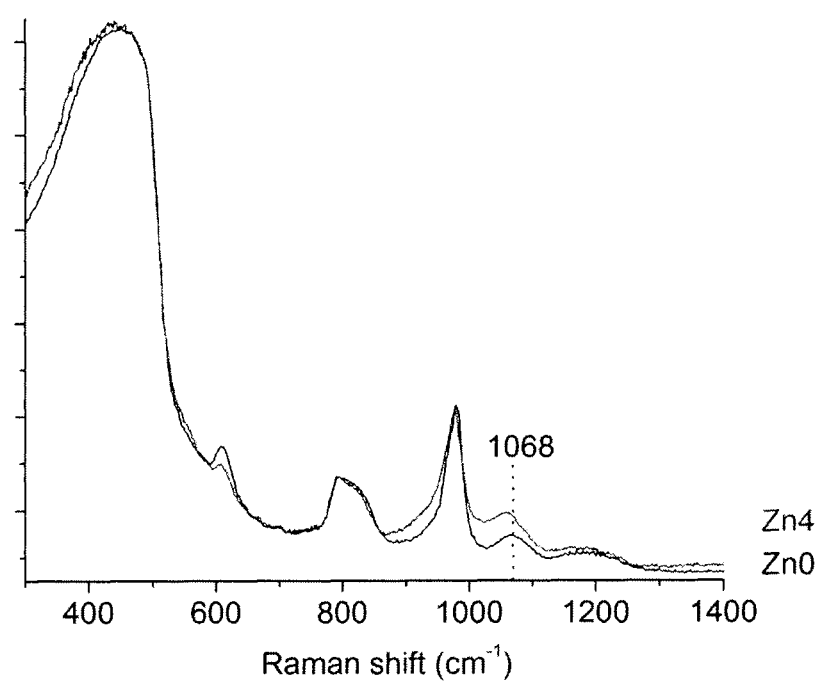
FIG. 3 shows in situ UV Raman spectra obtained in helium flow at room temperature of Zn-free silica (ZnO) and 4 wt % Zn(II) on silica (Zn4) after calcination at 300° C.
Figures 6A, 6B, 6C:
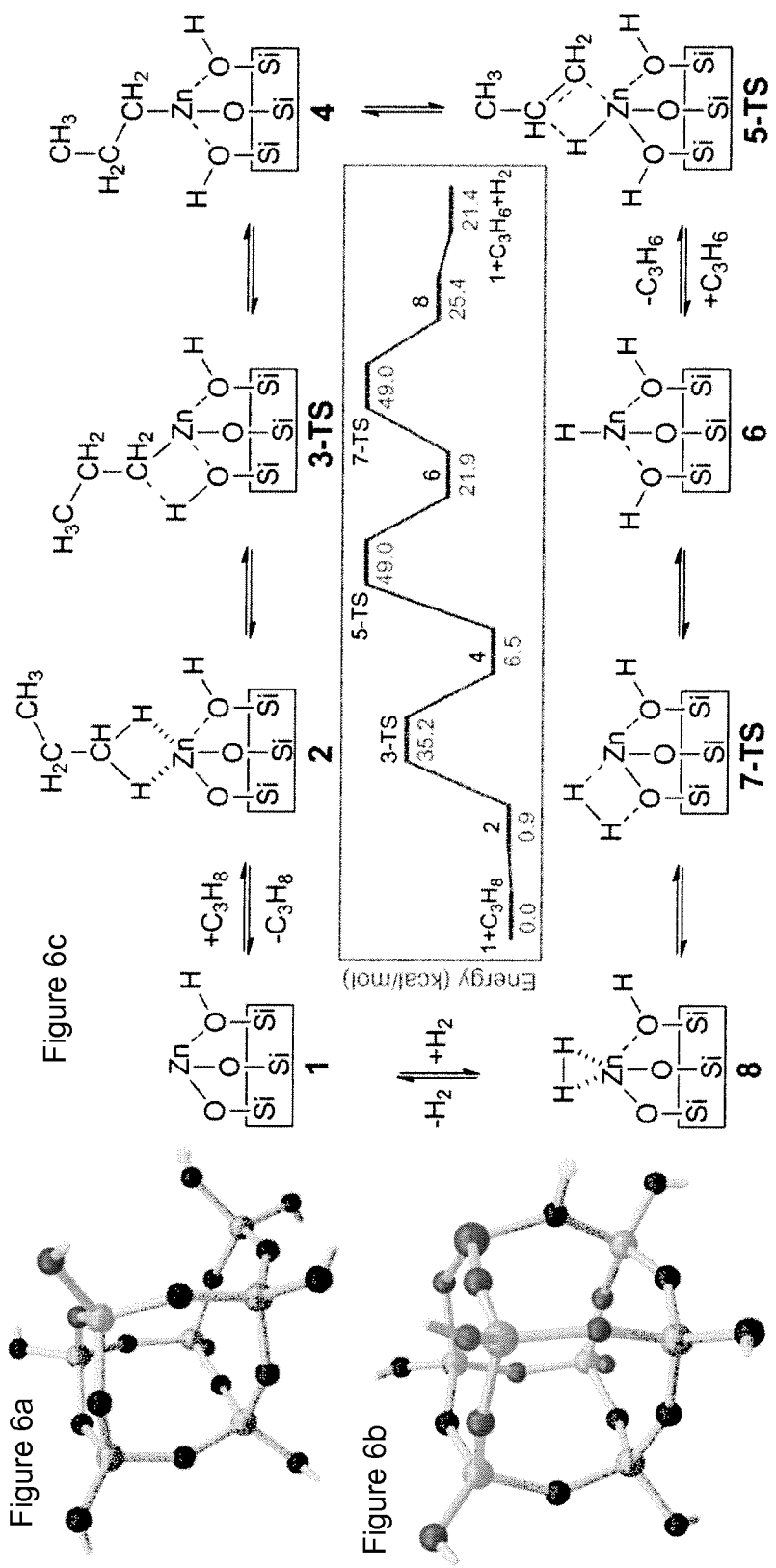
FIGS. 6a-6c are a series of schematics showing.
Figure 11:
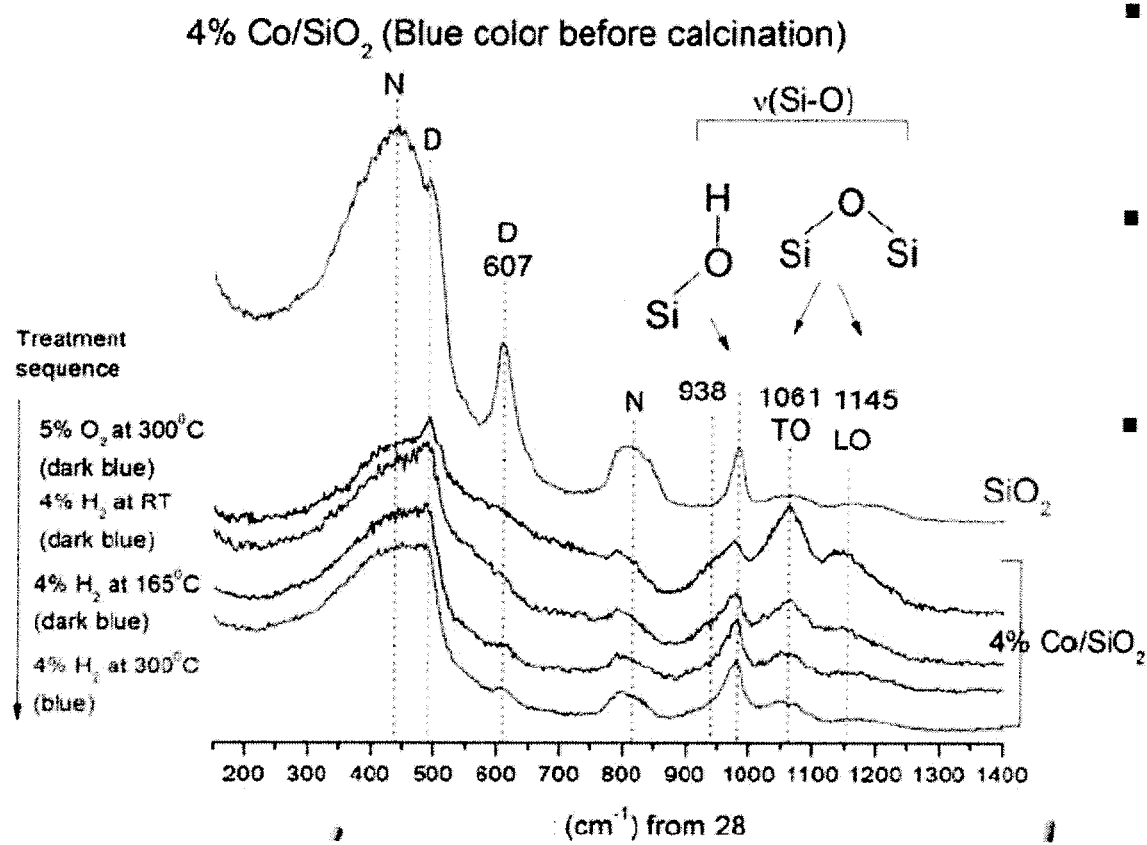
FIG. 11 shows the Raman spectra results used in determining the structure and placement of the Co(II) ion.
Figure 12:
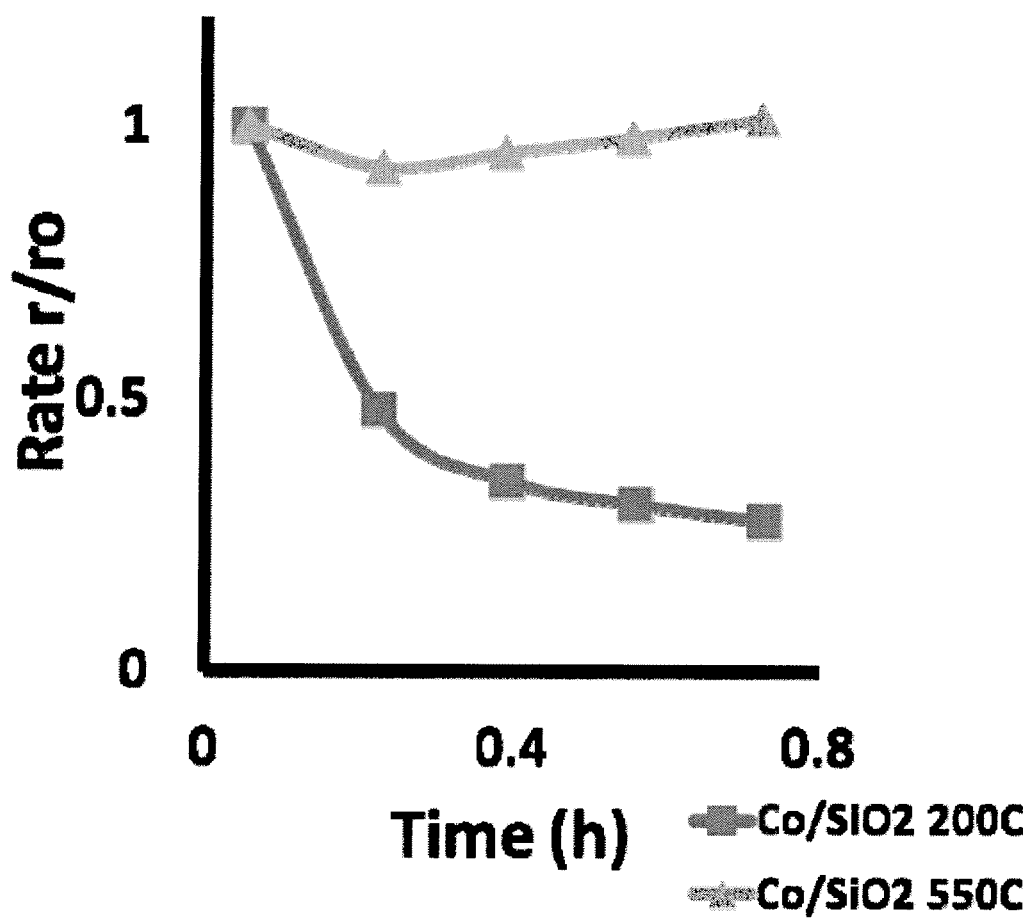
FIG. 12 is a histogram showing the effect of temperature on the rate of propylene hydrogenation with a Co(II) catalyst.

When 4 wt % Zn is added to $SiO_2$, the defect (D2) vibrational band centered at 608 cm$^{-1}$ due to a 3-member siloxane ring (FIGS. 2, 3) significantly decreases in intensity. Also, transverse Si—O—Si network vibration centered ~1068 cm$^{-1}$ redshifts by 10 cm$^{-1}$. The degree of redshift matches well with the DFT result obtained for the Zn coordination to 3-membered ring. Note that the longitudinal network vibration centered ~1200 cm$^{-1}$ the other defect vibration (D1) ~490 cm$^{-1}$, and 5-/6-membered ring network vibrations ~450 cm$^{-1}$ do not show any noticeable spectral change. Therefore, Raman results, as shown in FIG. 11, demonstrate that Zn primarily binds to the D2 defect site, i.e., 3-membered ring of $SiO_2$. The 10 cm$^{-1}$ redshift in frequency of transverse asymmetric Si—O—Si vibrations also supports the binding of Zn to the D2 site. A proposed structure of the tetrahedral coordinated, single site Zn(II) is shown in FIG. 6b. This structure is consistent with the calculated stable binding of tetrahedral zinc in the corner vacancy of the $SiO_2$.

After synthesis of $Zn/SiO_2$, the vibrational band at 607 cm-1 (604 cm-1 calculated) due to a 3-member siloxane ring, FIG. 6a, is absent suggesting that the Zn(II) ion binds selectively at this surface site. In addition, there is an enhancement in the intensity of the 980 cm-1 band due to Si—OH, perhaps indicating resonance enhancement of this band. A proposed structure of the tetrahedral coordinated, single site Zn(II) is shown in FIG. 6b. This structure is consistent with the calculated stable binding of tetrahedral zinc in the corner vacancy of the $SiO_2$. The remaining Raman bands on $SiO_2$ are largely unchanged upon zinc coordination.

Although the Zn ions are only present in the +2 oxidation state, the $Zn(II)/SiO_2$ displays catalytic hydrogenation activity at temperatures above about 150° C. Table 3 presents the kinetic rates for propylene hydrogenation at 200° C. determined under differential conversion of 8.2%. The $SiO_2$ support is unreactive at these conditions. During the 16-h test period, there is little deactivation with the final conversion about 0.97 that of the initial conversion and no products other than propane were observed.

TABLE 4

Turn-over frequencies for propylene hydrogenation at 200° C. and propane dehydrogenation at 550° C. of the $Zn(II)/SiO_2$ catalyst

| | Hydrogenation TOF (h$^{-1}$) | | | Dehydrogenation TOF (h$^{-1}$) | | |
|---|---|---|---|---|---|---|
| Catalyst | t = 0 h | t = 12 h | (r/r$_0$) | t = 0 h | t = 12 h | (r/r$_0$) |
| $Zn/SiO_2$ | 0.303 | 0.295 | 0.974 | 0.772 | 0.394 | 0.511 |

Figure 4:
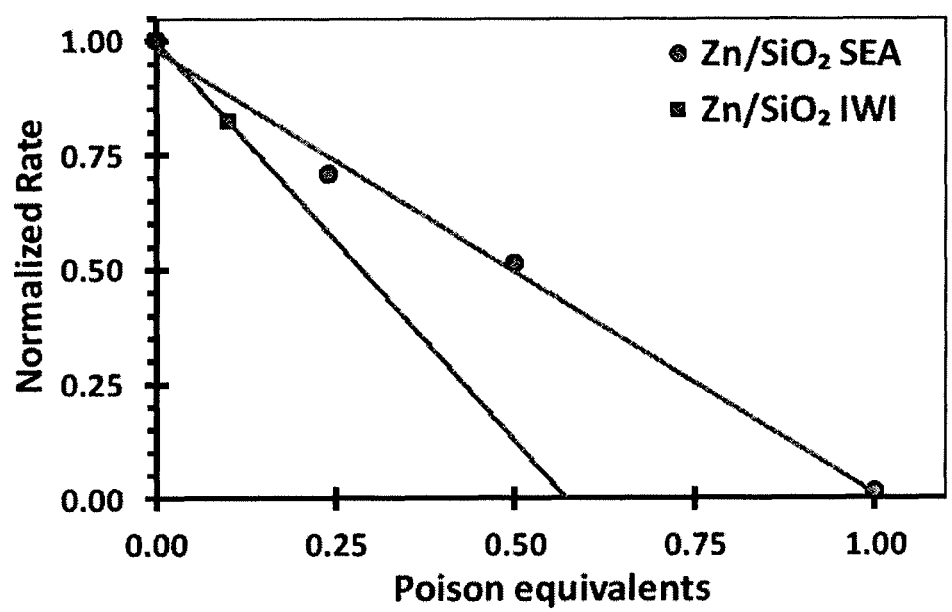
FIG. 4 is a line graph showing the effect of propanol and pyridine poisoning on the hydrogenation rate.

The active hydrogenation sites are readily poisoned by alcohols and amines, thus the number of catalytic sites could be determined by adsorption of these poisons. FIG. 4 shows that there is a linear decrease in the normalized rate per equivalent of added poison with either isopropanol or pyridine providing additional evidence that nearly every Zn(II) ion is equally catalytically active and the Zn phase is 100% dispersed. The turnover frequencies in Table 1 were based on this assumption. The sample poisoned with one equivalent of pyridine per zinc was also examined by infrared spectroscopy before and after the hydrogenation reaction. The strong infrared bands at 1612 and 1452 cm$^{-1}$ and the smaller band at 1493 cm$^{-1}$ are consistent with pyridine adsorbed on Lewis acid sites. In the absence of Zn(II) ions, silica does not adsorb pyridine at 200° C. Furthermore, the complete loss of hydrogenation activity with a one molar equivalent of pyridine indicates that these Lewis acid sites are the catalytic sites.

Figures 5A, 5B:
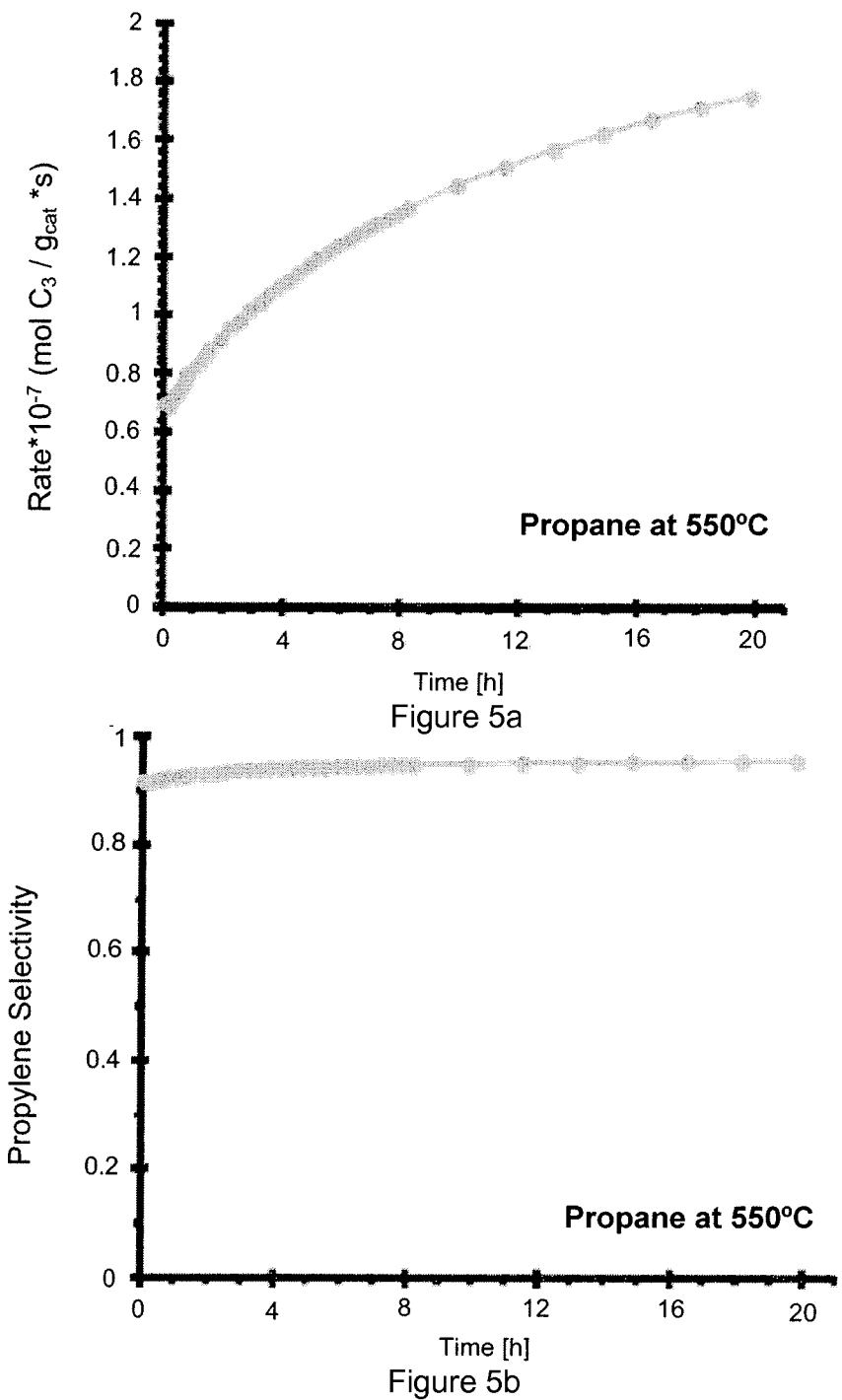
FIGS. 5a and 5b shows two histograms illustrating.

$Zn(II)/SiO_2$ is also catalytically active for propane dehydrogenation at temperatures above 550° C. At reaction temperatures above 600° C., however, there is a significant contribution to the products from thermal cracking. As a result, the catalyst was tested at the lower temperature (and under differential conversion of 4.4%) in order to more clearly determine the intrinsic selectivity. During the 16 h test, the $Zn(II)/SiO_2$ catalyst exhibits a slow decrease in the propane conversion and rate of the $Zn(II)/SiO_2$ to about half the initial conversion; while the thermal cracking rate, e.g., of $SiO_2$, is unchanged, FIG. 5a.

The propane dehydrogenation products were methane, ethylene and propylene. For thermal cracking (with or without silica), the propylene, ethylene and methane selectivities were 40.2, 30.0 and 29.8, respectively at a conversion of 0.6%. For the $Zn(II)/SiO_2$ the propylene selectivity at propane conversions from 5 to 20% (the equilibrium conversion at 550° C. was ca. 37%[2] was much higher with lower selectivities to ethylene and methane, 95.3, 2.4 and 2.3, respectively. The propylene selectivity of the Zn(II)/SiO$_2$ remains high throughout the catalyst test, FIG. 5b. The propylene selectivity was similarly high at higher propane conversions.

Example 3

Structural and Functional Characterization

Lewis acid catalysts are not known to catalyze hydrogenation or dehydrogenation reactions; thus, second order Moller-Plesset (MP2) calculations of potential reaction pathways and intermediates were performed and are summarized schematically in FIG. 6. Although the synthesized Zn is tetrahedrally coordinated, at high temperature there is loss of oxygen coordination, presumably as water, to form a 3-coordinate, Lewis acidic zinc. On this reactive center, the C—H bond in propane is heterolytically cleaved to form a zinc alkyl and bridging hydroxyl group (intermediate 4), consistent with observations by Kokes, et al. of stoichiometric alkane activation by bulk ZnO. The resulting β-hydride elimination (5-TS) to form propene and a zinc hydride is the calculated rate-limiting step. Zinc alkyls are known to be particularly resistant to β-hydride elimination; however the catalysis temperature is well above the documented reaction for zinc alkyls. A separately computed pathway for C—C cracking was found. However, the transition state is at least 20 kcal/mol higher in energy than the for the dehydrogenation rate-limiting step, consistent with the observed high selectivity of Zn/SiO$_2$ for alkane dehydrogenation over C—C bond cleavage.

For the olefin hydrogenation pathway, H$_2$ heterolytically reacts at the Zn(II) Lewis acid producing a Zn—H and SiOH. Olefin insertion occurs at the Zn—H bond and proton transfer to the Zn-alkyl bond completes the catalytic cycle. The cycle proceeds without a change in the Zn oxidation state. In both reaction directions, the coordinatively unsaturated Lewis acid attacks a sigma bond, C—H or H—H, rather than coordinating to a lone pair of electrons as in typical Lewis acid catalyzed reactions.

Electron deficient metal centers have been shown to interact with sigma bonds by catalyzing a four-centered transition state in σ-bond metathesis and the related σ-complex-assisted metathesis (σ-CAM) mechanism. However, the proton is directly transferred from one ligand to another during the reaction. In these cases, the resulting reaction is degenerate scrambling of hydrogen between hydrocarbon or other ligands. In addition to σ-bond metathesis and heterolytic splitting of C—H bonds has also been observed with metal hydroxides and across metal-carbon multiple bonds. Again, alkane exchange is the observed reaction performed by these species. Catalytically mediating a substrate transformation rather than degenerate exchange at the metal center remains a significant challenge for alkane activation. Lewis acidic Zn/SiO$_2$ demonstrates this ability, representing a distinct advantage over other, related catalysts. Finally, the strong Si—O bonds prevents further reaction of the catalytic site to loose water, reduce the zinc site, aggregate into nanoparticles, or otherwise decompose under the high temperatures necessary for alkane dehydrogenation.

The reaction pathway proposed above is also reminiscent of that for the Brönsted acid (BA) catalyzed monomolecular cracking of alkanes at low conversion. In zeolites, for example, the proton attacks C—C bonds and to a lesser extent C—H bonds. The reaction is thought to occur by a three center-two-electron transition state with the reactive proton and an alkane sigma bond. The initial alkane activation transition state calculated and proposed in FIG. 6c contains a similar polarization of the C—H σ bond, resulting in heterolytic cleavage to form the zinc alkyl. There are a number of significant differences between the LA catalyzed reactions of alkanes and olefins those of BA. First, the LA primarily activates alkane C—H bonds while the BA reacts nearly statistically with C—C or C—H σ bonds. As a result, the primary reaction catalyzed by Zn/SiO$_2$ produces almost exclusively H$_2$ and olefin, while on zeolite catalysts the C—C cleavage leads primarily to lower molecular weight alkanes in addition to olefins. Second, the Zn(II) Lewis acid is unreactive with the olefin product and olefins readily undergo secondary reactions in zeolites such as oligomerization, skeletal isomerization, bimolecular cracking, aromatic formation, etc. Cleavages that produce methane are especially unproductive since BA catalysts cannot reincorporate it into the catalytic cycle. The low reactivity of olefin products with the LA means that the dehydrogenation selectivity is high at all conversions; while for BA alkane dehydrogenation is only observed at low conversions. Finally, while BA affect alkane dehydrogenation, albeit at low conversion, they have not been reported to catalyze olefin hydrogenation unlike what is observed for the Zn(II)/SiO$_2$ Lewis acid catalyst.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A catalyst for use in olefin production comprising one or more single-atom Lewis acid metal ions selected from the group consisting of Zn tetrahedrally coordinated on the surface of an amorphous silica support in which a tetrahedrally coordinated Zn(II) ion is bonded at a corner vacancy of SiO2 of the amorphous silica support wherein said catalyst selectively cleaves C—H bonds over C—C bonds in the conversion of alkanes to alkenes.

2. The catalyst of claim 1, wherein the catalyst is a heterogeneous, single-site Zn(II) catalyst, in which the tetrahedrally coordinated Zn(II) ion is bonded to the silica support at 3-membered ring siloxane sites.

3. The catalyst of claim 1, wherein the catalyst is not redox-active.

4. The catalyst of claim 1, wherein the catalyst has a selectivity of greater than 75% for C—H activation.

5. The catalyst of claim 1, wherein the catalyst has a selectivity of greater than 90% for C—H activation.

6. The catalyst of claim 1, wherein the catalyst has a selectivity of greater than 95% for C—H activation.

7. The catalyst of claim 1, wherein the catalyst retains catalytic activity for longer than 1 hour.

8. The catalyst of claim 1, wherein the catalyst retains catalytic activity for longer than 12 hours.

9. The catalyst of claim 1, wherein the catalyst retains catalytic activity for longer than 24 hours.

* * * * *